(12) United States Patent
Whitkin et al.

(10) Patent No.: US 11,797,706 B2
(45) Date of Patent: Oct. 24, 2023

(54) MOBILE DEVICE NETWORK TRAFFIC MODIFICATION AND USER BASED RESTRICTIONS ON DATA ACCESS

(71) Applicant: HEALTH2047, INC., San Francisco, CA (US)

(72) Inventors: Josh O. Whitkin, Hunters Hill (AU); Justin James Klein, San Francisco, CA (US); Bernard Pierce Mangold, Mercer Island, WA (US); Jack Stockert, Los Altos, CA (US); Michael James Walker, Portland, OR (US)

(73) Assignee: Health2047, Inc., Menlo Park, CA (US)

( * ) Notice: Subject to any disclaimer, the term of this patent is extended or adjusted under 35 U.S.C. 154(b) by 399 days.

(21) Appl. No.: 15/429,070

(22) Filed: Feb. 9, 2017

(65) Prior Publication Data
US 2017/0228504 A1 Aug. 10, 2017

Related U.S. Application Data

(60) Provisional application No. 62/293,268, filed on Feb. 9, 2016.

(51) Int. Cl.
*G06F 21/60* (2013.01)
*G06F 21/71* (2013.01)
(Continued)

(52) U.S. Cl.
CPC ........ *G06F 21/6245* (2013.01); *G06F 21/604* (2013.01); *G06F 21/71* (2013.01);
(Continued)

(58) Field of Classification Search
CPC ....... G06F 21/604; G06F 21/71; G06Q 40/08; H04L 63/08
See application file for complete search history.

(56) References Cited

U.S. PATENT DOCUMENTS

| 8,380,631 B2 | 2/2013 | Dala et al. |
| 8,396,804 B1 | 3/2013 | Dala et al. |

(Continued)

OTHER PUBLICATIONS

Donovan, Fred "HHS Pushes for Changes to HIPAA Privacy Rule, 42 CFR Part 2" Health IT Security Jul. 30, 2018; available at: https://healthitsecurity.com/news/hhs-to-propose-changes-to-hipaa-privacy-rule-42-cfr-part-2 (Year: 2018).*

(Continued)

*Primary Examiner* — Andrew B Whitaker
*Assistant Examiner* — Brendan S O'Shea
(74) *Attorney, Agent, or Firm* — Knobbe, Martens, Olson & Bear, LLP

(57) ABSTRACT

Systems and techniques are disclosed for mobile device network traffic modification and user identity based restrictions on data access. One of the methods includes a user device receiving a request to enter a restricted mode, the restricted mode enforcing compliance of rules associated with electronic personal health information (ePHI). A user interface presented on the user device is updated according to restricted mode. Functionality of the user device is constrained based on the restricted mode, with information generated during the restricted mode being encrypted on the user device.

21 Claims, 3 Drawing Sheets

(51) Int. Cl.
*G06Q 40/08* (2012.01)
*G06F 21/62* (2013.01)
*H04L 9/40* (2022.01)
*G16H 10/60* (2018.01)

(52) U.S. Cl.
CPC ............ *G06Q 40/08* (2013.01); *G16H 10/60* (2018.01); *H04L 63/08* (2013.01)

(56) References Cited

U.S. PATENT DOCUMENTS

| | | | |
|---|---|---|---|
| 8,849,718 | B2 | 9/2014 | Dala et al. |
| 8,943,168 | B2 | 1/2015 | Weisner et al. |
| 9,495,511 | B2 | 11/2016 | Harrington et al. |
| 9,618,967 | B2 | 4/2017 | Brown et al. |
| 10,021,087 | B2 | 7/2018 | Karimzadeh et al. |
| 10,699,356 | B2 | 6/2020 | Thesman |
| 10,733,266 | B2 | 8/2020 | Whitehurst |
| 10,789,662 | B1 | 9/2020 | Wartenfeld et al. |
| 10,803,977 | B2 | 10/2020 | Sanmugalingham |
| 11,282,594 | B2 | 3/2022 | Cohen et al. |
| 11,404,146 | B2 | 8/2022 | Keen et al. |
| 2012/0235930 | A1* | 9/2012 | Lazaridis ............ H04M 1/7243 345/173 |
| 2013/0042295 | A1* | 2/2013 | Kelly ................... G06F 21/53 726/1 |
| 2013/0345530 | A1* | 12/2013 | McRoberts .......... A61B 5/0022 600/323 |
| 2014/0278534 | A1* | 9/2014 | Romeo ................. G16H 10/60 705/3 |
| 2015/0012287 | A1* | 1/2015 | Vucovich ........... G06Q 30/0267 705/2 |
| 2015/0121464 | A1* | 4/2015 | Hughes, Jr. ........... H04L 63/105 726/4 |
| 2015/0244743 | A1* | 8/2015 | Jagad .................... G06F 21/577 726/1 |
| 2015/0248230 | A1* | 9/2015 | Mark ..................... H04L 67/10 715/747 |
| 2015/0347682 | A1 | 12/2015 | Chen et al. |
| 2016/0125550 | A1 | 5/2016 | Joao et al. |
| 2016/0317077 | A1 | 11/2016 | Sillay |
| 2016/0342744 | A1 | 11/2016 | Joao |
| 2018/0089394 | A1 | 3/2018 | Hyde et al. |
| 2019/0378608 | A1 | 12/2019 | Nusimow et al. |

OTHER PUBLICATIONS

Rios, Joy "HIPAA Security for iPhones" Health Information Technology, Oct. 10, 2013; available at: https://www.hitechanswers.net/hipaa-security-iphones/ (Year: 2013).*

"HIPAA Compliance Checklist" by HIPAA Journal, available at: https://www.hipaajournal.com/hipaa-compliance-checklist/ (Year: 2018).*

"Summary of the HIPAA Security Rule" by HHS.gov, available at: https://www.hhs.gov/hipaa/for-professionals/security/laws-regulations/index.html (Year: 2013).*

"Hash Function" Wikipedia, archived Nov. 6, 2015 available at: https://web.archive.org/web/20151106165617/http://en.wikipedia.org/wiki/Hash_Junction (Year: 2015).*

"Smartphones" Breach Prevention, Yale University; as archived Mar. 3, 2015; available at: https://web.archive.org/web/20150303072035/https://hipaa.yale.edu/security/breach-prevention/smartphones (Year: 2015).*

* cited by examiner

MOBILE DEVICE NETWORK TRAFFIC MODIFICATION AND USER BASED RESTRICTIONS ON DATA ACCESS

BACKGROUND

Protected health information of patients can include specific identifiers such as name, address, date information, social security numbers and medical record numbers and so on. This protected health information is statutorily required to be treated with special care by medical professionals or other covered entities. For example, protected health information in an electronic form may be maintained in an encrypted state, and access to the protected health information can be tightly controlled. With the advent of mobile devices utilized by medical professionals for both their personal and career lives, utilizing mobile devices can create problems with respect to conforming to statutory requirements as related to protected health information.

SUMMARY

Particular embodiments of the subject matter described in this specification can be implemented so as to realize one or more of the following advantages. A medical professional's mobile device (for example, smart phone, tablet, wearable device) can be easily toggled between a personal or normal mode and a protected mode that complies with statutes related to protecting personal health information. An example statute is the Health Insurance Portability and Accountability Act (HIPAA), which in part requires covered entities to treat protected health information with special care. For example, the protected health information may be required to be encrypted, and access to, or sharing of, protected health information may include various constraints. To ensure compliance with these statutory rules, a mobile device can include functionality to be placed in a normal mode, in which the normal functionality of the mobile device is enabled, and a protected mode, in which all functionality of the mobile device conforms to statutory requirements.

As will be described, to enter and/or exit the protected mode, strong authentication can be required, such as biometric information coupled with global navigation satellite system (GNSS) information to ensure that a medical professional is only accessing protected health information at work, and so on. Additionally, the mobile device can automatically encrypt, and keep separate from access while in public mode, any protected health information. In this way, the features described herein solve technical problems associated with protecting and controlling access to protected health information. The mobile device can automatically analyze network traffic to ensure compliance with statutory requirements. For example, the mobile device can determine that an application executing on the mobile device is attempting to transmit protected health information, and the mobile device can block the transmission, or automatically filter the transmission to remove any protected health information.

The details, including optional details, of one or more embodiments of the subject matter of this specification are set forth in the accompanying drawings and the description below. Other optional features, aspects, and advantages of the subject matter will become apparent from the description, the drawings, and the claims.

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

DETAILED DESCRIPTION

Figure 1:
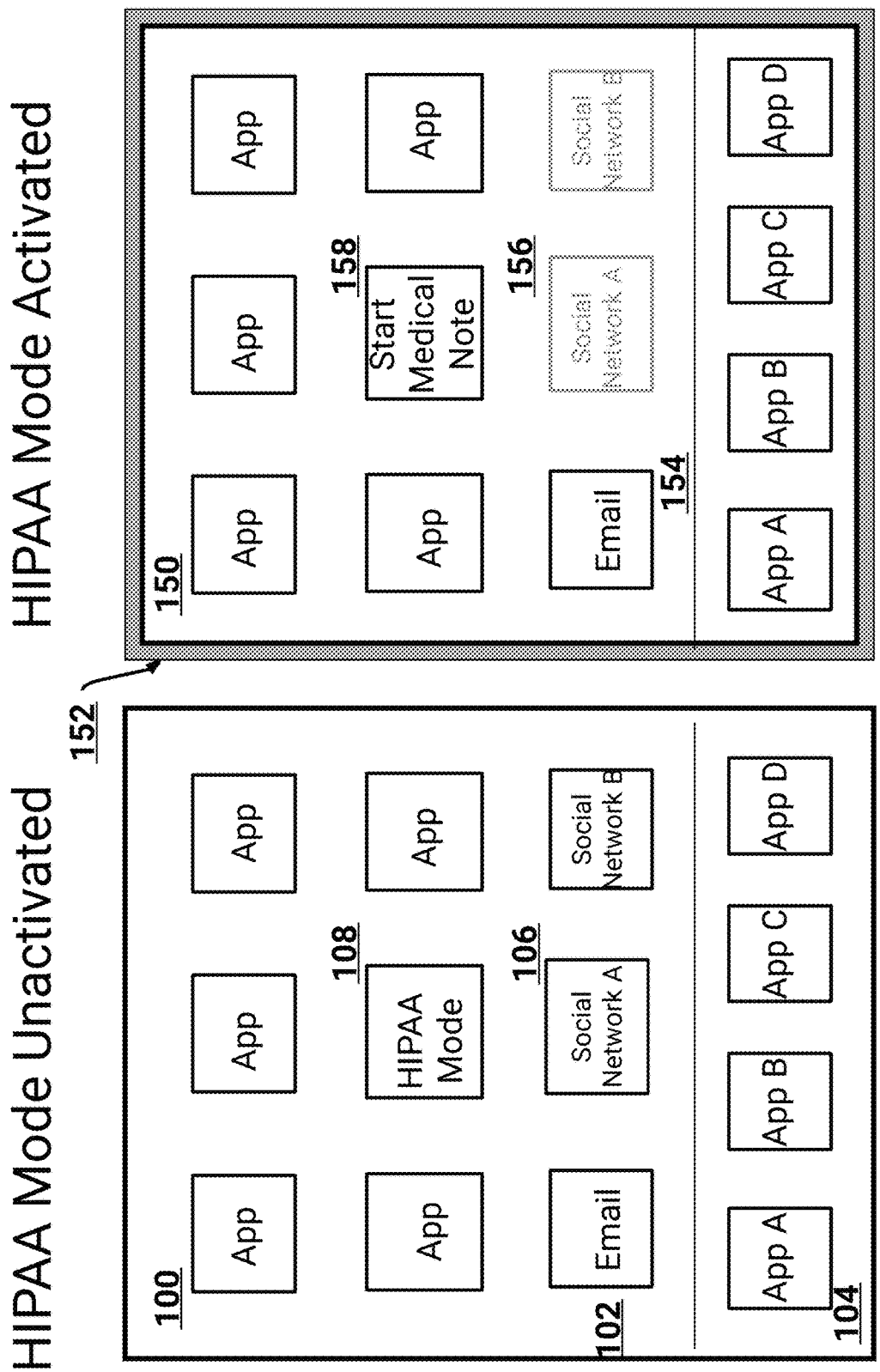
FIG. 1 illustrates a user device operating in two modes.

Although particular embodiments are described herein, other embodiments, including embodiments that do not provide all of the benefits and features set forth herein, will be apparent to those of ordinary skill in the art.

This specification describes modifying user devices to conform to statutory requirements associated with electronic protected health information (hereinafter referred to as ePHI). An example statute is the Health Insurance Portability and Accountability Act (HIPAA), and while reference is made to HIPAA, or a HIPAA mode, it should be understood that other statutes, rules, ethical guidelines, and so on, may be taken into account when the features described herein are implemented. Examples of ePHI can include one or more of Names, Geographic data, All elements of dates, Telephone numbers, FAX numbers, Email addresses, Social Security numbers, Medical record numbers, Health plan beneficiary numbers, Account numbers, Certificate/license numbers, Vehicle identifiers and serial numbers including license plates, Device identifiers and serial numbers, Web URLs, Internet protocol addresses, Biometric identifiers (for example, retinal scan, fingerprints), Full face photos and comparable images, Any unique identifying number, characteristic or code, and so on.

As will be described in more detail, a user device can be placed in a HIPAA mode, and functionality of the user device can be modified or constrained to conform to statutory rules and/or ethical guidelines of handling ePHI. For example, particular applications can be disabled when the user device is placed in the HIPAA mode. As an example of disabling applications, the user device can cause icons associated with the disabled applications to be un-selectable by a user (for example, greyed out). Another example of disabling applications can include monitoring network traffic from the user device, for example via packet sniffing and/or address resolution protocol spoofing, and blocking network traffic associated with the disabled applications. Another example of HIPAA mode can include particular applications being disabled and replaced with functionally-equivalent applications that are HIPAA compliant. As another example, functionality of particular applications can be modified when in the HIPAA mode. For example, a messaging application can store information in an encrypted form when in the HIPAA mode, and/or the messaging application can provide messages only to particular contacts (for example, medical professionals). An application can be an application obtained from an electronic application store (for example, an 'app'), and which executes on a user device.

Therefore, in contrast to forcing medical professionals to utilize a single application that may be designed to be HIPAA compliant for all purposes (for example, messaging, email, taking images, and so on), this specification adjusts functionality of the user device. Through adjusting use of the user device, the features described herein solve technical problems. For example, network traffic being provided from, or coming into, the user device may be monitored, filtered, and/or blocked. As an example, an outside system may analyze received network traffic from the user device, and may scan for ePHI included in the network traffic. The outside system may then block or filter this ePHI. In this way, HIPAA compliance can be tightly controlled, without forcing medical professionals to merely use a single application and give up their preferred applications.

FIG. 1 illustrates a user device operating in two modes. As described above, a user device can include a smart phone, tablet, wearable device, and so on, and can be associated with a software platform. Example software platforms include iOS, ANDROID, WINDOWS MOBILE (for example, Windows 10 Mobile, Windows Phone), and so on. As will be described, functionality of the user device can be modified or adjusted when placed in a particular protected mode, referred to herein as a HIPAA mode.

User interface 100 illustrates an example of a user device displaying applications that can be selected by a user of the user device. For example, the user interface 100 includes three user applications 102, which may be applications obtained from an electronic application store, positioned above native applications 104, which may be applications native to an operating system platform associated with the user device. As illustrated, user interface 100 is associated with a HIPAA mode not being activated, and can therefore represent a covered entity operating his/her user device outside of work. For example, a covered entity can be a medical professional, and medical professional can operate his/her user device when handling personal matters outside of work.

User interface 150 illustrates an example of the user device with the HIPAA mode being activated. For example, a user of the user device can interact with the user device to place the user device in HIPAA mode. Examples of interactions can include interacting with a button or physical object on the user device, which upon interaction can place the user device in HIPAA mode. An additional example can include the user interacting with an application (for example, application 108) in the user interface 150 to indicate a request to enter HIPAA mode. Alternatively, the user can use a gesture on a lock or main screen of the device to enter HIPAA mode. For example, swiping up from a particular spot on the screen can initiate the HIPAA mode. To place the user device in HIPAA mode, the user device can prompt the user to input authentication information, biometric information, and so on. As an example, the user can input a user name and password, press his/her thumb or finger on a fingerprint reader, point a camera of the user device for facial recognition purposes, a near field communication (NFC) card can be placed near the user device, and so on.

An additional example of placing the user device in the HIPAA mode can include the user device obtaining present global navigation system satellite (GNSS) coordinates, and determining that the user device is at, or within a threshold distance of, a hospital, medical practice group, or anywhere indicated as being associated with ePHI. For example, a geofence may be maintained around a hospital, and as the user device crosses the geofence, the user device may automatically be triggered to be placed in HIPAA mode. Optionally, the user device can prompt the user to input authentication information, for example as described above.

Upon entering the HIPAA mode, the user device can present an indication of HIPAA compliance. For example, the user interface 150 can adjust a border 152 of the user interface 150 to be a particular color. Additionally, an icon may be presented at a location in the user interface 150 (for example, at a top portion of the user interface 150). In this way, a user of the user device can quickly ascertain that his/her user device is HIPAA compliant.

Additionally, upon entering the HIPAA mode particular applications can be made inaccessible to the user, for example application 106 becomes an inaccessible application 156 in HIPAA mode. This inaccessible application 156 is indicated in the illustration as being greyed out. Other visual representations of the inaccessibility can be utilized, for example the application 156 can be removed from the user interface 150 or the application 156 can be crossed out, and so on. The user device can maintain information indicating the applications, for example application 106, that are to be inaccessible when in HIPAA mode. The user device can therefore access the information, and cause the indicated applications to be inaccessible.

Optionally, when placed in the HIPAA mode, the user device can connect to one or more virtual private networks (VPNs) such that all network traffic is routed through one or more servers associated with the VPNs. The servers may analyze network traffic being provided to, or received from, the user device, and can block network traffic associated with the inaccessible applications. As an example, the server can perform a packet sniffing process and/or address resolution protocol spoofing, to determine whether the network traffic is associated with inaccessible applications. In this way, if the operating system platform associated with the user device makes it difficult, or impossible, to modify a visual representation of an inaccessible application, the application's functionality can still be blocked.

Applications that may be indicated as being HIPAA compliant can be presented unmodified in the user interface 150. For example, a secure email client 154 can be presented the same as in user interface 100, and the user of the user device can utilize the secure email client 154 as normal. However, other applications may be modified to be HIPAA compliant, and the user device can modify functionality of these applications. For example, a messaging application may be modified to place it in a secure messaging mode such that all messages are provided via encrypted methods. Additionally, as messages are created, sent, and/or received, the messaging application may store messages in an encrypted format or may immediately delete them. In this way, upon exiting the HIPAA mode, the messages created, sent, and/or received while in HIPAA mode, can be made inaccessible to the user. Optionally, the user device can identify whether ePHI is included in the messages, and can encrypt or delete them upon a positive identification. As an example, the user device can obtain indications of patients while in the HIPAA mode (for example, any ePHI associated with patients), and compare the indications to information included in messages. As another example, a camera application may allow the user to obtain images via a camera of the user device. However, the images may be automatically encrypted, provided to an outside server via an encrypted channel, or deleted upon exiting the HIPAA mode. In this way, the images may be inaccessible to the user when not in the HIPAA mode, and if they are encrypted, may become accessible as the user returns to the HIPAA mode at a later time. For information being provided to an outside server for storage, the outside server may maintain an encrypted version of the information, and the outside server can provide the encrypted versions to the user device on a subsequent entry into the HIPAA mode.

The user interface 150 may swap particular applications with functionally equivalent, or similar, applications. For example, a particular video chat client may not HIPAA compliant, and the user interface 150 may instead present a different video chat client that is HIPAA compliant. The user device may present the different video chat client in a same location as the particular video chat client, such that the user can easily identify and select the video chat client.

Furthermore, particular applications may be only accessible in the HIPAA mode. For example, application 158 is related to recording medical notes. This example application 158 may be inaccessible to the user while not in the HIPAA mode, and information associated with the application 158 may be encrypted on the user device. Additionally, the encrypted information may be stored on an outside server, and as the user device is placed in the HIPAA mode the information can be provided to the user device or provided in response to requests received from the application 158 for information.

Optionally, when the user device is in the HIPAA mode, no information can be stored locally. As described above, optionally the information may also be encrypted and stored locally. Additionally, if the data is stored locally, the data can be made accessible only when in HIPAA mode (for example, the data may have access restrictions placed on it such that it may not be visible when not placed in HIPAA mode).

To exit the HIPAA mode, the user may be required to provide authentication information, for example as described above. Additionally, location information of the user device may be utilized. As an example, the user may not be able to exit HIPAA mode while located within a threshold distance of a hospital, medical practice, and so on.

Figure 2:
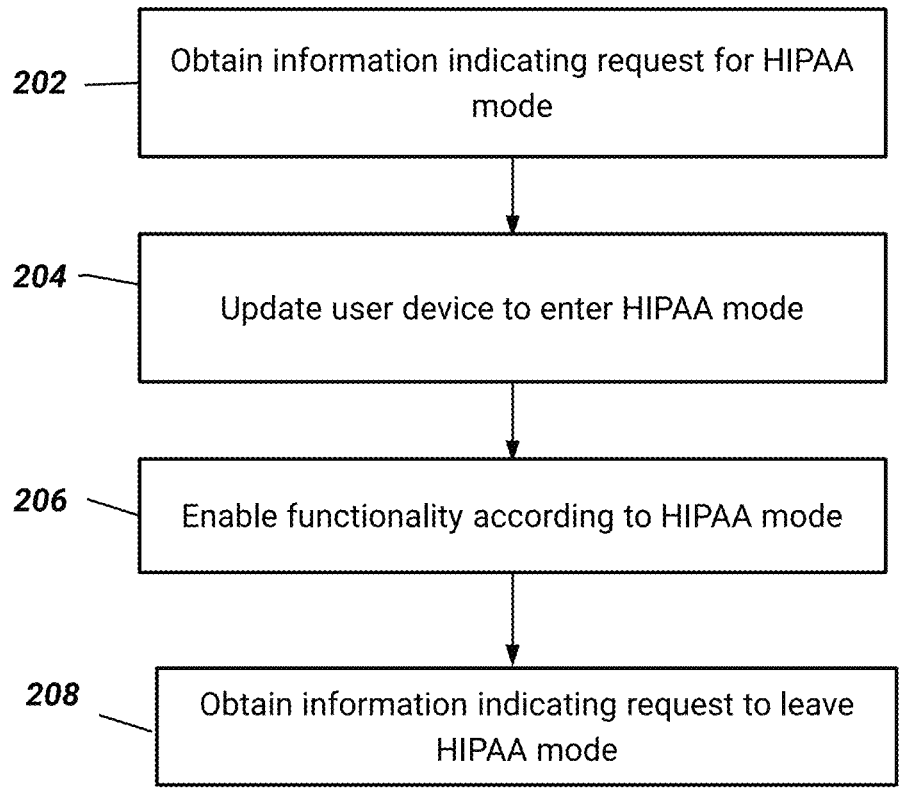
FIG. 2 illustrates a flowchart of an example process for utilizing a HIPAA mode.

FIG. 2 illustrates a flowchart of an example process 200 for utilizing a HIPAA mode. For convenience, the process 200 will be described as being performed by a user device of one or more processors.

The user device obtains information indicating that it is to place the user device in HIPAA mode (block 202). As described above, the user device can operate normally, and the user can place the user device in HIPAA mode. Optionally, the user device may determine automatically that it is to be placed in HIPAA mode, for example based on location information. The user device may further require authentication information, and in combination with location information may require a weaker authentication form. For example, if the user device is at a hospital known to employ the user, or the user device is navigating along a route known to be associated with the user's work commute, the user device may prompt the user for a keycode (for example, 4-digit keycode). Optionally, the user device may require more complex authentication information, such as biometric information, user account information (for example, user name, password), and so on.

The user device updates to enter HIPAA mode (block 204). Upon determining that HIPAA mode is to be entered, the user device updates user interfaces presented to the user via a display (for example, a touch screen display). As an example, the user device may cause particular applications to be inaccessible, may swap applications for other applications that are HIPAA compliant, and so on. Optionally, the user device may block particular notifications from being presented to the user. For example, if the user device is in a locked state, a normal behavior of the user device may be to present notifications on the lock screen. While in the HIPAA mode, the user device may block these notifications from being sent such that no information is visible without the user device being an unlocked state. Optionally, the notifications may be filtered to remove ePHI. As an example, the user device may obtain information associated with patients, and may remove any ePHI corresponding to them from the notifications.

The user device enables functionality according HIPAA mode (block 208). The user device can enable (for example, constrain) functionality such that all actions the user can perform are HIPAA compliant. Subsequently, the user device may receive a request to exit HIPAA mode (block 210). As described above, the user of the user device may interact with the user device to request that the user device return to a normal operating mode, which may be based on a location of the user.

Optionally, the user device may include an application associated with detecting and removing ePHI that is stored on the user device. The application may scan all locally stored data on a regular or on-demand basis. The application can optionally optimize performance by searching common locations, formats and APIs from common application. For example, common application can include social network applications, mail application, calendar applications, contact applications, and so on.

The application can remove ePHI from local storage. For example, the application may activate upon user selection, or may be activated periodically in time, upon an exit of the HIPAA mode, and so on. Rules for identifying ePHI can be obtained, for example a rule can indicate that if a doctor's user device has any text messages from any patient phone number, which is ePHI. However, the rule can indicate that if the patient is on a 'consent-given' list, then that is not ePHI. Optionally, ePHI may be identified based on signatures, or hashes, of the ePHI as determined by an outside system. For example, as described above an outside system may store ePHI associated with patients. The outside system may provide signatures, hashes, or checksums, of ePHI such as names, addresses, and so on, and the user device may compare these signatures, hashes, or checksums, to signatures, hashes, or checksums, of information it has locally stored. That is, the user device may generate signatures, hashes, checksums, in a same manner as the outside system. For any match, the user device may remove the matching information. Optionally, if the user device is connected via a VPN to the outside system, the outside system may analyze received network traffic and identify whether ePHI is included. If identified, the outside system may remove the ePHI, disable all network traffic from an associated application, and so on, such that ePHI is not being provided from the user device.

Figure 3:
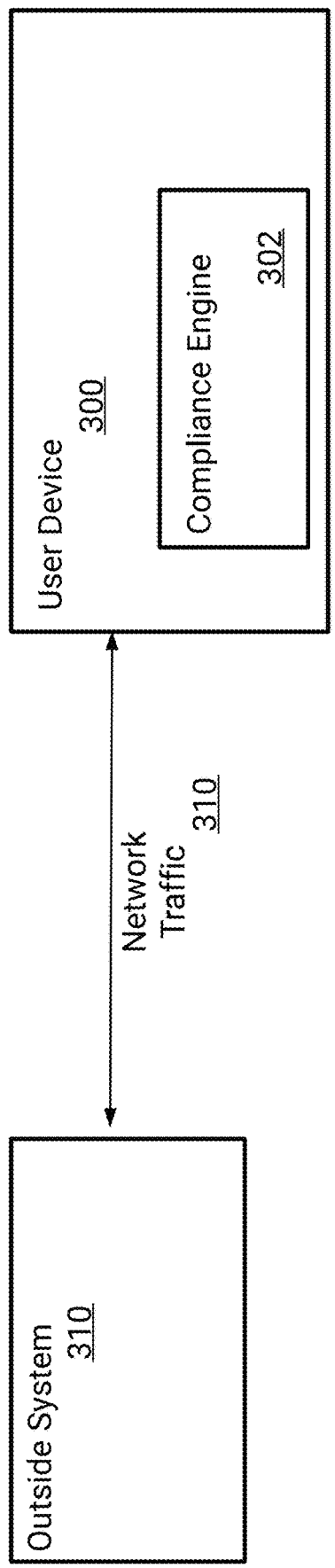
FIG. 3 illustrates a block diagram of a user device in communication with an outside system.

FIG. 3 illustrates a block diagram of a user device 300 in communication with an outside system 320. As described above, the user device 300 can be a mobile device, a tablet, a wearable device, and can present a graphical user interface to a user of the user device. The graphical user interface can present options associated with selecting applications, for example applications obtained from an electronic application store. The user device 300 can include a compliance engine 302 that can modify functionality associated with the user device 300 to enable the user device to be placed in a HIPAA mode, for example the functionality described above. Optionally, the compliance engine 302 can be modified operating system executing on the user device 300, or the compliance engine 302 can ensure that particular applications are not accessible or that the particular applications have their functionality modified as described above. For example, an outside system 310 may receive network traffic 310 from the user device 300 via a virtual private network connection. The outside system may block particular applications from being utilized (for example, block associated network traffic 310), ensuring that HIPAA compliance is maintained. Additionally, as described above, the compliance engine 302 may remove any ePHI stored locally on the user device 300.

Additional Embodiments

Each of the processes, methods, and algorithms described in the preceding sections may be embodied in, and fully or partially automated by, code modules executed by one or more computer systems or computer processors comprising computer hardware. The code modules (or "engines") may be stored on any type of, one or more, non-transitory computer-readable media (for example, a computer storage product) or computer storage devices, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, for example, volatile or non-volatile storage.

In general, the terms "engine" and "module", as used herein, refer to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on one or more computer readable media, such as a compact discs, digital video discs, flash drives, or any other tangible media. Such software code may be stored, partially or fully, on a memory device of the executing computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

User interfaces described herein are optionally presented (and user instructions may be received) via a user computing device using a browser, other network resource viewer, a dedicated application, or otherwise. Various features described or illustrated as being present in different embodiments or user interfaces may be combined into the same embodiment or user interface. Commands and information received from the user may be stored and acted on by the various systems disclosed herein using the processes disclosed herein. While the disclosure may reference to a user hovering over, pointing at, or clicking on a particular item, other techniques may be used to detect an item of user interest. For example, the user may touch the item via a touch screen, or otherwise indicate an interest. The user interfaces described herein may be presented on a user terminal, such as a laptop computer, desktop computer, tablet computer, smart phone, virtual reality headset, augmented reality headset, or other terminal type. The user terminals may be associated with user input devices, such as touch screens, microphones, touch pads, keyboards, mice, styluses, cameras, etc. While the foregoing discussion and figures may illustrate various types of menus, other types of menus may be used. For example, menus may be provided via a drop down menu, a tool bar, a pop up menu, interactive voice response system, or otherwise.

The various features and processes described herein may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y or Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y or at least one of Z to each be present.

While certain example embodiments have been described, these embodiments have been presented by way of example only, and are not intended to limit the scope of the disclosure. Thus, nothing in the foregoing description is intended to imply that any particular element, feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

The accompanying claims and their equivalents are intended to cover such forms or modifications as would fall within the scope and spirit of certain of the inventions disclosed herein.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated herein, it should be noted that the use of particular terminology when describing certain features or aspects of the invention should not be taken to imply that the terminology is being re-defined herein to be restricted to including any specific characteristics of the features or aspects of the invention with which that terminology is associated.

What is claimed is:

1. Non-transitory computing storage media storing instructions that, when executed by a personal mobile computing device, cause the personal mobile computing device to implement operations for a health-data protected operation mode which prevents health information from being accessed or sent in an unauthorized manner, wherein the operations comprise:
    receiving a request, by the personal mobile computing device, to enter the health-data protection mode, the health-data protection mode constraining functionality of the personal mobile computing device;
    updating a user interface presenting a plurality of applications accessible via the personal mobile computing device, wherein updating comprises:
    updating a visual representation of a first application of the plurality of applications, the updated visual representation being presented in the user interface and indicating inaccessibility of the first application,
    presenting a new application that is positioned at a same location in the user interface as a second application of the plurality of applications, wherein the second application is disabled during the health-data protection mode and removed from the user interface, and wherein the new application replaces the second application during the health-data protection mode and is associated with same functionality,
    wherein visual representations of a remaining of the plurality of applications are unaltered and remain presented in the user interface as being accessible; and
    constraining the functionality of the personal mobile computing device based on the health-data protection mode such that selection of the plurality of applications is constrained, wherein information generated during the health-data protection mode is encrypted on the personal mobile computing device.

2. The computer storage media of claim 1, wherein the operations further comprise:
    in response to receiving the request, prompting a user of the personal mobile computing device for authentication information.

3. The computer storage media of claim 2, wherein authentication information comprises one or more of user account information, biometric information, and location information of the personal mobile computing device.

4. The computer storage media of claim 2, wherein the request is triggered based on (1) a first location of the personal mobile computing device being within a particular geofence, (2) information indicating a user of the personal mobile computing device is associated with a second location within the particular geofence or information indicating the user is navigating along a route associated with the second location, and (3) receipt of correct authentication information provided in response to the prompting.

5. The computer storage media of claim 1, wherein constraining functionality of the personal mobile computing device comprises:
    modifying functionality associated with one or more of the applications based on the health-data protection mode.

6. The computer storage media of claim 5, wherein a particular application is a messaging application, and wherein the messages sent or received while the personal mobile computing device is in the health-data protection mode are inaccessible upon the personal mobile computing device leaving the health-data protection mode.

7. The computer storage media of claim 1, wherein constraining functionality comprises modifying one or more applications to be inaccessible in the health-data protection mode, and wherein the operations further comprises:
    establishing a virtual private network connection with an outside system, the outside system receiving all network traffic being provided to, or being provided from, the personal mobile computing device, such that the outside system is configured to block network traffic associated with the inaccessible applications.

8. The computer storage media of claim 1, wherein the operations further comprise:
    receiving a request to leave the health-data protection mode; and
    upon leaving the health-data protection mode, deleting the particular health information.

9. The computer storage media of claim 8, wherein deleting the particular health information comprises:
    obtaining, from an outside server, one or more hash values generated based on health information of one or more patients associated with a user of the personal mobile computing device;
    generating hash values based on information locally stored on the personal mobile computing device; and
    deleting information locally stored on the personal mobile computing device with hash values corresponding to the obtained hash values.

10. The computer storage media of claim 1, wherein upon exiting of the health-data protection mode particular health information is identified for deletion from local storage based, at least in part, on hash information generated from information stored in local storage.

11. The computer storage media of claim 1, wherein the received request adjusts a normal operating mode of the personal mobile computing device to the health-data protection mode, wherein the second application is accessible during the normal operating mode, and wherein based on leaving the health-data protection mode, updating the user interface to return to the normal operating mode.

12. A method implemented by a user device of one or more processors, the method comprising
- receiving a request to enter a health data protection mode, the health data protection mode constraining functionality of the user device;
- updating a user interface presenting a plurality of applications accessible via the user device, wherein updating comprises:
  - updating a visual representation of a first application of the plurality of applications, the updated visual representation being presented in the user interface and indicating inaccessibility of the first application,
  - swapping a second application of the plurality of applications with a new application associated with same functionality, wherein the new application is included in the user interface at a same location as the second application, and wherein the second application is disabled during the health data protection mode and removed from the user interface,
  - wherein visual representations of a remaining of the plurality of applications are unaltered and remain presented in the user interface; and
- constraining the functionality based on the health data protection mode such that selection of the plurality of applications is constrained, wherein information generated during the health data protection mode is encrypted on the user device.

13. The method of claim 12, further comprising:
- in response to receiving the request, prompting a user of the user device for authentication information.

14. The method of claim 13, wherein authentication information comprises one or more of user account information, biometric information, and location information of the user device.

15. The method of claim 12, wherein constraining functionality of the user device comprises:
- modifying functionality associated with one or more of the applications based on the health data protection mode.

16. The method of claim 15, wherein a particular application is a messaging application, and wherein the messages sent or received while the user device is in the health data protection mode are inaccessible upon the user device leaving the health data protection mode.

17. The method of claim 12, wherein constraining functionality comprises modifying one or more applications to be inaccessible in the health data protection mode, and wherein the method further comprises:
- establishing a virtual private network connection with an outside system, the outside system receiving all network traffic being provided to, or being provided from, the user device, such that the outside system is configured to block network traffic associated with the inaccessible applications.

18. The method of claim 12, wherein the method further comprises:
- receiving a request to leave the health data protection mode; and
- upon leaving the health data protection mode, deleting particular health information.

19. The method of claim 18, wherein deleting the particular health information comprises:
- obtaining, from an outside server, one or more hash values generated based on health information of one or more patients associated with a user of the user device;
- generating hash values based on information locally stored on the user device; and
- deleting information locally stored on the user device with hash values corresponding to the obtained hash values.

20. The method of claim 18, wherein upon exiting of the health-data protection mode particular health information is identified for deletion from local storage based, at least in part, on hash information generated from information stored in local storage.

21. The method of claim 12, wherein exiting of the health data protection mode is constrained based on a location of the user device.

* * * * *

UNITED STATES PATENT AND TRADEMARK OFFICE
CERTIFICATE OF CORRECTION

| | |
|---|---|
| PATENT NO. | : 11,797,706 B2 |
| APPLICATION NO. | : 15/429070 |
| DATED | : October 24, 2023 |
| INVENTOR(S) | : Josh O. Whitkin |

It is certified that error appears in the above-identified patent and that said Letters Patent is hereby corrected as shown below:

On the Title Page

Column 1 (Item (72) Inventors), Line 3, delete "Pierce" and insert -- Pierre --.

Signed and Sealed this
Second Day of July, 2024

Katherine Kelly Vidal
*Director of the United States Patent and Trademark Office*